US007504228B2

(12) United States Patent
Kojic et al.

(10) Patent No.: US 7,504,228 B2
(45) Date of Patent: Mar. 17, 2009

(54) INTEGRIN LINKED KINASE MODULATION OF MONOCYTE ACTIVATION

(75) Inventors: Ljiljana Kojic, Vancouver (CA); Patricia M. Logan, Vancouver (CA); Jeffery J. Wheeler, Surrey (CA); Kymberley L. Sutton, Surrey (CA); Gabriel Bela Kalmar, Richmond (CA)

(73) Assignee: QLT Inc., Vancouver, British Columbia (CA)

( * ) Notice: Subject to any disclaimer, the term of this patent is extended or adjusted under 35 U.S.C. 154(b) by 139 days.

(21) Appl. No.: 10/163,599

(22) Filed: Jun. 5, 2002

(65) Prior Publication Data
US 2005/0220779 A1 Oct. 6, 2005

Related U.S. Application Data

(60) Provisional application No. 60/296,181, filed on Jun. 5, 2001.

(51) Int. Cl.
| | |
|---|---|
| *G01N 33/00* | (2006.01) |
| *G01N 33/53* | (2006.01) |
| *C12Q 1/68* | (2006.01) |
| *A61K 31/415* | (2006.01) |
| *A61K 33/26* | (2006.01) |
| *A61K 31/47* | (2006.01) |
| *A61K 39/395* | (2006.01) |
| *C12N 9/12* | (2006.01) |

(52) U.S. Cl. .................. 435/7.24; 435/7.92; 435/6; 435/375; 435/194; 435/7.1; 514/406; 514/150; 514/310; 424/146.1

(58) Field of Classification Search ............... 514/150, 514/151, 404; 435/375
See application file for complete search history.

(56) References Cited

U.S. PATENT DOCUMENTS

| | | | |
|---|---|---|---|
| 4,563,476 A * | 1/1986 | Chang et al. ........... 514/459 |
| 5,010,058 A * | 4/1991 | Ronsen et al. ........... 514/23 |
| 5,132,300 A * | 7/1992 | Volkmann et al. ...... 514/192 |
| 5,811,300 A * | 9/1998 | Sullivan et al. ........ 435/366 |
| 6,001,622 A | 12/1999 | Dedhar et al. |
| 6,013,782 A | 1/2000 | Dedhar et al. |
| 6,177,273 B1 | 1/2001 | Bennett et al. |
| 6,214,813 B1 | 4/2001 | Zhang et al. |
| 2003/0013640 A1* | 1/2003 | Kojic et al. ................ 514/2 |

OTHER PUBLICATIONS

D'Acquisto et al., Local administration of transcription factor . . . , Gene therapy, abstract only (2000), vol. 7 (20), pp. 1731-1737.*

(Continued)

*Primary Examiner*—Elizabeth C. Kemmerer
*Assistant Examiner*—Zachary C Howard
(74) *Attorney, Agent, or Firm*—Bozicevic, Field & Francis LLP; Pamela J. Sherwood (57) ABSTRACT

Methods are provided to specifically modulate the activation of monocytes and/or macrophages. Administration of integrin linked kinase (ILK) blocking agents; compounds that otherwise prevent the binding of natural ILK ligands to ILK; or compounds that prevent expression of, or signaling through ILK exert an anti-inflammatory effect by inhibiting iNOS and COX-2 expression, at the level of transcription by suppressing the activation of NF-κB. The modulation of activation through ILK is used to regulate immune processes at targeted sites, for example to decrease undesirable inflammatory responses.

5 Claims, 3 Drawing Sheets

OTHER PUBLICATIONS

D'Acquisto et al., "transcription factor decoy oligodeoxynucleotides ti . . ." Naunyn-Schmiederberg's Archives of Pharmacology, Abstract only (2001), vol. 364(5), pp. 422-429.*

Surh et al., Molecular mechanisms underlying chemopreventive activities . . . , Mutation Research, abstract only, 2001, vol. 480-481, pp. 243-268.*

Zampini et al., Integrin-mediated upregulation . . . , Surgical Forum, abstract only, 2000, vol. 51, pp. 225-227.*

McGilvray et al., MAP-kinase dependent induction . . . , Journal of Surgical Research, abstract only, 1998, vol. 80(2), pp. 272-279.*

Summary of US4563476(1986), US5010058(1991), US5811300(1998) and US5132300(1992).*

Shimizu et al, Histochemical analysis of macrophage migration . . . , (Abstract only), Histochemistry and Cell biology, 2002, vol. 118(3), pp. 251-257.*

Guha et al, 2001. Cellular Signalling. 13: 85-94.*

Riedemann et al, 2003. Nature Medicine. 9(5): 517-524.*

Dobrovolskaia et al, 2002. Microbes and Infection. 4: 903-914.*

Triantafilou et al, 2002. Trends in Immunology. 23(6): 301-304.*

Bosca et al, 2005. Toxicology. 208: 249-258.*

Kleinert et al, 2004. European Journal of Pharmacology. 500: 255-266.*

Phillips, 2001. J Pharm Pharmacology. 53: 1169-1174.*

Monick et al, 2002. Journal of Biological Chemistry. 32992-33000.*

Iezzi et al 2007. Current Pharmaceutical Design. 13: 1715-1721.*

Schneeman et al, 2007. Journal of Leukocyte Biology. 81: 579.*

Birkenkamp et al (2000. Experimental Hematology. 28: 1230-1249).*

Macmicking, J. et al. (1997), *Ann. Rev. Immunol.*, 15:323-350.

Albina et al., (1998), *Cancer Metastasis Rev.*, 17:39-53.

Xie et al., (1994), *J. Biol. Chem.*, 269:4705-4708.

Nathan et al., (1995), *Cell*, 82:873-876.

* cited by examiner

INTEGRIN LINKED KINASE MODULATION OF MONOCYTE ACTIVATION

BACKGROUND OF THE INVENTION

The process of inflammation is mediated by both circulating and resident monocytes and the cells with which they interact, e.g. vascular endothelium and smooth muscle cells. The appearance of inflammatory cells at the site of tissue injury is a characteristic of almost any immune-related disease. Infiltrating monocytes mediate the initiation and progression of damage by direct cytotoxicity, the secretion of soluble factors, or by regulating the immune response. These include the expression of adhesion molecules on monocytes and underlying vascular endothelium and the release of cytokines, chemokines, tissue-destructive metalloproteases and reactive oxygen species.

During the early, specific phase of the host defense response, production of interferon-gamma (IFN-γ) by natural killer cells plays an important role in setting off acute inflammation, primarily because of the activating effects of IFN-γ on the adhesive properties of endothelial cells and on mediator production by mononuclear phagocytes. High-level production of IFN-γ during this phase of host defense is a hallmark of a T-helper 1 (TH1)-type reaction, characterized by activation of the antimicrobial activity of macrophages and by triggering a cascade of inflammatory reactions.

Macrophages play a significant role in the host defense mechanism. These cells reside in various tissues and are among the first cells of any organ to be exposed to infectious agents and to become activated in response to an insult. Upon activation macrophages participate actively in the onset of inflammation by releasing cytokines that amplify the initial inflammatory response. These inflammatory cytokines include: bioactive lipids (prostaglandins and leukotrienes), reactive oxygen intermediates (ROI) and reactive nitrogen intermediates (RNI) that exert cytotoxic effects against pathogens and tumor cells. Activation of the host immune system by Gram-negative bacteria can be reproduced in vitro by incubation of cells with lipopolysaccharide (LPS, a predominant glycolipid in the outer membrane of Gram-negative bacteria) and IFN-γ acting as a pro-inflammatory cytokine. LPS and IFN-γ stimulate macrophage cells to an activated state, priming them for antimicrobial activity, increased killing of intracellular pathogens, and antigen processing and presentation to lymphocytes. These biological effects are mediated by up-regulating MHC class II expression and increasing release of nitric oxide (NO) and pro-inflammatory cytokines.

Several early signaling pathways have been identified in response to LPS-induced activation of macrophages, including mitogen-activated protein kinase (MAPK), c-Jun N-terminal kinase, and p38/stress-activated protein kinase as well as various members of the Src family of protein tyrosine kinases and Vav. LPS, commonly known as a second messenger, synergizes with IFN-γ in the stimulation of macrophages by activating NF-κB which results in the transcriptional up-regulation of a number of genes involved in the cell-mediated immune response. As a result of this activation sequence, macrophages express enzymes involved in inflammation, such as inducible NO-synthase (iNOS, the enzyme responsible for NO synthesis), cyclooxygenase-2 (COX-2, the enzyme responsible for the high output synthesis of PGs), and matrix metalloproteinases.

Nitric oxide is a highly reactive nitrogen radical implicated in multiple biologic processes ranging from endothelium-dependent relaxation to long-term potentiation in neuronal synapses and macrophage tumoricidal activity. Its formation is regulated by a family of enzymes, known as nitric oxide synthase (NOS). At least three distinct, but functionally and structurally related, isoforms of NOS have been identified in mammalian cells.

The macrophage iNOS regulates NO synthesis over a period of several hours following stimulation with LPS. Changes in NO production in iNOS-expressing cells usually correlate with similar changes in iNOS mRNA levels, indicating that a major part of iNOS regulation occurs at the level of transcription. The promoter region of the iNOS gene contains several consensus sequences for the binding of transcriptional factors, such as NF-κB, activator protein-1 (AP-1), and various other proteins. Of the latter proteins, members of the NF-κB family appear to be essential components for enhanced iNOS gene expression in macrophages exposed to the active components of the LPS endotoxin. In unstimulated cells, NF-κB is retained in the cytoplasm by binding to IκB. The NF-κB-IκB complex is released in response to activated signaling cascades, upon which NF-κB translocates to the nucleus, and activates responsive gene elements.

As a mediator of macrophage cytotoxicity, NO is proven to be beneficial when released in physiological amounts. However, despite its beneficial role in host defense mechanisms, excessive NO production by activated macrophages has been implicated in the pathogenesis of several acute and chronic inflammatory diseases including arthritis, inflammation of the upper respiratory tract, lung inflammation, and the enhancement of human immunodeficiency virus (HIV) replication in primary human macrophages. Also, iNOS-dependent tissue destruction has been seen in several rodent autoimmunity models, such as experimental allergic encephalitis (EAE) and uveitis (EAU), inflammatory arthritis, and immune complex glomerulonephritis. Furthermore, it has been demonstrated that iNOS promotes tumor angiogenesis and metastasis.

Therefore, the regulation of NO production by activated macrophages, and consequently inflammation, is critical to limiting damage to host tissues without compromising the immune response elicited by the host to combat infectious agents.

In view of the importance of monocyte activation in immune responses, the further characterization and manipulation of the pathways regulating activation are of great interest.

Relevant Literature

The role of nitric oxide in immune function is discussed in MacMicking et al. (1997) *Annu. Rev. Immunol.* 15:323; Albina and Reichner (1998) *Cancer Metastasis Rev.* 17:39; Xie et al. (1994) *J. Biol. Chem.* 269:4705; and Nathan (1995) *Cell* 82:873.

SUMMARY OF THE INVENTION

The activation of monocytes and macrophages is prevented by the administration of integrin linked kinase (ILK) blocking agents; compounds that otherwise prevent the binding of natural ILK ligands to ILK; or compounds that prevent expression of, or signaling through, ILK. ILK inhibitors exert an anti-inflammatory effect by inhibiting iNOS and COX-2 expression, at the level of transcription by suppressing the activation of NF-κB. Release of NO plays a critical role in mediating inflammatory responses. The modulation of activation through ILK is used to regulate immune processes at targeted sites, for example to decrease undesirable inflammatory responses.

BRIEF DESCRIPTION OF THE DRAWINGS

FIG. 1. Effects of YS 51 on iNOS protein expression in lung tissues and on plasma ILK analogs of iNOS and COX-2 protein expression. The ability of a number of different ILK inhibitors to moderate the inflammatory response in vitro was compared to the positive control compound, SB203580 (p38 MAPK inhibitor). Primary macrophages were stimulated with LPS and INF-γ. ILK inhibitor compounds were applied to the activated macrophages. Twenty hours post-treatment, iNOS and COX-2 protein expression was determined. Results were normalized to the expression of actin. Many of the ILK inhibitor compounds were more effective than the positive control in reducing iNOS and COX-2 protein expression.

FIG. 2. ILK inhibitors suppress LPS-INF-γ induced NO production and NF-κB activation. The 3T3 cells were transiently transfected with a transcription reporter construct containing the NF-κB-Luc gene element, and the activity of NF-κB was measured 24 h later. Transfected 3T3 cells treated with ILK inhibitors exhibited a dose-dependent decrease of NF-κB activation when compared to untreated cells. The reduction of transcriptional activity from the NF-κB promoter correlated with NO production.

FIG. 3. ILK inhibitors suppressed VEGF-induced in vitro tube formation of HUVECs. HUVEC cells were stimulated with rVEGF (1 ng/ml) and thereafter were treated either with the vehicle alone, a positive control with the chemical formula (Z)-3-[2,4-dimethyl-5-(2-oxo-1,2-dihydroindol-3-ylidenemethyl)-1H-pyrrol-3-yl]propionic acid, or with various ILK inhibitors. After 5 hours of incubation at 37° C., the three-dimensional organization of the cells was examined using an inverted photomicroscope. The cells were fixed with Crystal Violet (0.05% in 20% ethanol) and digitally photographed. A complete network of tubes was observed when HUVEC cells were stimulated with VEGF. ILK inhibitors either induced cell connections without a complete network of tubes formation, or demonstrated a significant anti-angiogenic effect, blocking the growth, morphogenic organization and formation of normal capillary-like structures.

DETAILED DESCRIPTION OF THE EMBODIMENT

Inhibitors of integrin linked kinase (ILK) suppress the activation of monocytes and macrophages by inhibiting expression of inducible nitric oxide synthase (iNOS) and COX-2, thereby blocking the release of NO and other pro-inflammatory factors. Compounds that modulate the triggering activity of ILK are administered systemically or locally to alter the activation of monocytes and macrophages. Such activation may be associated with disease, e.g. inflammation, allergic reactions, etc., or may be part of normal biological homeostasis. ILK is a mediator of signaling through an integrin receptor, and can link the external binding of integrins to intracellular pathways. By intervening at this point of the integrin signaling pathway, the physiological localization of immune effector and regulatory cells can be altered, thereby providing therapeutic benefit to a patient.

Local administration that provides for a prolonged localized concentration, which may utilize sustained release implants or other topical formulation, is of particular interest. In vivo uses of the method are of interest for therapeutic and investigational purposes. In vitro uses are of interest for drug screening, determination of physiological pathways, and the like.

The mononuclear phagocyte system is comprised of both circulating and fixed populations of cells. The circulating component is the monocyte. Upon migration into tissues these are referred to as histiocytes or tissue macrophages. The major fixed macrophages include: Sinusoidal lining cells of the spleen, lymph nodes, liver, and bone marrow; connective tissue histiocytes; mobile macrophages on serosal surfaces; alveolar macrophages within the lung; microglia in the nervous system; and mesangial macrophages within renal glomeruli. Macrophages produce a variety of substances that are involved in inflammation.

Stimulation of macrophages with LPS and INF-γ induces NO production, expression of iNOS and COX-2 protein, as well as up-regulating IL-6 release, and activating the transcription factor NF-κB. Treatment of such stimulated macrophages with ILK inhibitors results in a dose-dependent inhibition of NO production and IL-6 release, accompanied by suppression of iNOS and COX-2 protein expression. Also, nuclear translocation of the transcription factor NFκB is reduced in a dose-dependent manner.

The anti-inflammatory properties of ILK inhibitors were assessed in an LPS and IFN-γ induced model of macrophage activation, including their capacity to affect NO production and IL-6 release. ILK inhibitors demonstrated an ability to block activated macrophages from producing NO and releasing IL-6, in a concentration dependent manner. At equivalent concentrations certain ILK compounds were more potent inhibitors of NO production and IL-6 release than dexamethasone and/or hydrocortisone. These inhibitory effects were treatment specific, as these compounds did not cause cytotoxic effects, as determined by a total protein assay after 24 h of treatment with compound. Nitric oxide and Prostaglandin $E_2$ are two pleiotropic mediators produced at inflammatory sites by the inducible enzymes iNOS and cyclooxygenase-2 (COX-2), respectively. Increased production of both mediators is associated with acute and in chronic inflammatory diseases.

The COX family of enzymes plays an essential role in tumor progression and supports angiogenesis by modulating the physiology of endothelial cells. A morphogenesis assay was used to compared the effect a potent inhibitor of angiogenesis and ILK inhibitors for their ability to inhibit the differentiation of HUVEC cells in vitro. Inhibition of ILK blocked the growth, morphogenic organization and formation of normal capillary-like structures in endothelial cells.

Integrin Linked Kinase

The integrin linked kinase, ILK, has previously been implicated in regulation of cell adhesion and fibronectin matrix assembly, and is herein shown to be involved in the activation of monocytes. The genetic sequence of human ILK is disclosed in U.S. Pat. Nos. 6,013,782; and 6,001,622, herein incorporated by reference. ILK is a serine threonine kinase having two functional domains, identified by comparison of the ILK sequence against those found in current protein databases. These are the catalytic domain, responsible for phosphotransferase activity (kinase domain), and a non-overlapping domain in the amino terminus, comprised of four contiguous ankyrin-like repeats. The function of ankyrin repeats in ILK is to mediate protein-protein interactions, although the ankyrin repeat domain is not required for the binding of ILK to integrin. ILK regulates integrin extracellular activity (ECM interactions) from inside the cell via its direct interaction with the integrin subunit (colloquially known as inside-out signaling).

ILK activity can be stimulated by phosphatidylinositol 3,4,5 trisphosphate in vitro. Both insulin and fibronectin can rapidly stimulate ILK activity in a phosphoinositide-3OH kinase (PI(3)K)-dependent manner. In addition, constitutively active PI(3)K activates ILK. The activated ILK can then inhibit the activity of glycogen synthase kinase-3 (GSK-3), contributing to ILK induced nuclear translocation of β-catenin. ILK can also phosphorylate protein kinase B (PKB/AKT) on serine-473, resulting in its activation, demonstrating that ILK is involved in agonist stimulated PI(3)K-dependent PKB/AKT activation.

ILK Modulating Agents

Agents that block ILK activity provide a point of intervention in an important signaling pathway. Numerous agents are useful in reducing ILK activity, including agents that directly modulate ILK expression, e.g. expression vectors, anti-sense specific for ILK, ILK specific antibodies and analogs thereof, small organic molecules that block ILK catalytic activity, etc.; and agents that affect ILK activity through direct or indirect modulation of [PtdIns(3,4,5)P$_3$] levels in a cell. For example, small molecule inhibitors of integrin linked kinase are described in U.S. Pat. No. 6,214,813, and in the Examples. Antisense inhibitors of ILK are described in U.S. Pat. No. 6,177,273, each herein incorporated by reference.

ILK modulating agents are molecules that specifically act as an agonist to enhance ILK biological activity; or that act as antagonists that block ILK biological activity, for example the interaction between ILK and its ligands. Such agents may activate the molecule through the ligand binding site, block the ligand binding site, etc. Blocking agents do not activate ILK triggering of adhesion. It will be understood by one of skill in the art that cross-reactivity and competition between different molecules is generally intended to refer to molecules having the same species of origin.

Drug screening can be used to identify agents that modulate ILK function. One can identify ligands or substrates that bind to, modulate or mimic the action of ILK. A wide variety of assays may be used for this purpose, including labeled in vitro protein-protein binding assays, electrophoretic mobility shift assays, immunoassays for protein binding, and the like. Knowledge of the 3-dimensional structure of ILK, derived from crystallization of purified recombinant ILK protein, leads to the rational design of small drugs that specifically inhibit ILK activity. These drugs may be directed at specific domains of ILK, e.g. the kinase catalytic domain, ankyrin repeat domains, pleckstrin homology domains, etc. Among the agents of interest for drug screening are those that interfere with the binding of cytoplasmic integrin tails to ILK; the kinase activity of ILK; binding of [PtdIns(3,4,5)P$_3$] to the PH domains of ILK and agents that inhibit the production of [PtdIns(3,4,5)P$_3$] by PI(3) kinase.

The term "agent" as used herein describes any molecule, e.g. protein or pharmaceutical, with the capability of altering or mimicking the physiological function of ILK. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of interest may detect agents that mimic or block ILK function, such integrin binding, kinase activity, down regulation of E-cadherin, up regulation of LEF-1, binding properties, etc. For example, an expression construct comprising a ILK gene may be introduced into a cell line under conditions that allow expression. The level of ILK activity is determined by a functional assay, as previously described. In one screening assay, candidate agents are added, and the formation of fibronectin matrix is detected. In another assay, the ability of candidate agents to enhance ILK function is determined.

Agents of interest for down-regulating ILK activity include direct blocking of [PtdIns(3,4,5)P$_3$] binding sites through competitive binding, steric hindrance, etc. Of particular interest are antibodies that bind to the PH domains, thereby blocking the site. Antibodies include fragments, e.g. F(Ab), F(Ab)', and other mimetics of the binding site. Such antibodies can be raised by immunization with the protein or the specific domain. Mimetics are identified by screening methods, as described herein. Analogs of [PtdIns(3,4,5)P$_3$] that compete for binding sites but do not result in activation of ILK are also of interest.

ILK activity is upregulated by the presence of the lipid [PtdIns(3,4,5)P$_3$]. The activity of ILK is manipulated by agents that affect cellular levels of [PtdIns(3,4,5)P$_3$], or that block the binding of [(PtdIns(3,4,5)P$_3$] to ILK. This lipid binds to specific amino acid residues in ILK. The amino acid sequence of ILK contains a sequence motif found in pleckstrin homology (PH) domains, which are involved in the binding of phosphatidylinositol phosphates. The activity of ILK is also down-regulated by inhibiting the activity of PI(3) kinase, thereby decreasing cellular levels of [PtdIns(3,4,5)P$_3$].

Agents of interest include inhibitors of PI(3) kinase, e.g. wortmannin, LY294002, etc. Physiologically effective levels of wortmannin range from about 10 to 1000 nM, usually from about 100 to 500 nM, and optimally at about 200 nM. Physiologically effective levels of LY294002 range from about 1 to 500 μM, usually from about 25 to 100 μM and optimally at about 50 μM. The inhibitors are administered in vivo or in vitro at a dose sufficient to provide for these concentrations in the target tissue.

The compounds of this invention can be incorporated into a variety of formulations for therapeutic administration. Particularly, agents that modulate ILK activity, or ILK polypeptides and analogs thereof are formulated for administration to patients for the treatment of ILK dysfunction, where the ILK activity is undesirably high or low. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The ILK may be systemic after administration or may be localized by the use of an implant that acts to retain the active dose at the site of implantation.

The compounds of the present invention can be administered alone, in combination with each other, or they can be used in combination with other known compounds. In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of infection, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 μg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which scope will be determined by the language in the claims.

It must be noted that as used herein and in the appended claims, the singular forms "a", "and", and "the" include plural referents unless the context clearly dictates otherwise. Thus, for example, reference to "a mouse" includes a plurality of such mice and reference to "the cytokine" includes reference to one or more cytokines and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for all relevant purposes, e.g., the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

Materials and Methods

Reagents. The iNOS inhibitor $N^G$-Monomethyl-L-arginine (L-NMMA) and murine rIFN-γ were purchased from Calbiochem, (San Diego, Calif.). Protein-free, phenol/water-extracted LPS (from *E. coli* serotype 0111:B4 0127:B8), Zymosan A, Dexamethasone and Hydrocortisone, sulfanilamide and N-(1-naphthyl)-ethylenediamine, were purchased from Sigma (St. Louis, Mo.). Human recombinant Vascular Endothelial Growth Factor VEGF was purchased from R&D Systems (Minneapolis, Minn.). Rabbit pAb against active (phosphorylated) extracellular signal-regulated kinase (ERK), as well as HRP-conjugated donkey anti-rabbit IgG were obtained from Promega (Madison, Wis.). ELISA dual-set kit for detection of IL-6 was purchased from PharMingen (San Diego, Calif.). Anti-murine iNOS/NOS type II and COX-2 antibodies were obtained from Transduction Laboratories (Lexington, Ky.).

Mice. Female, 6-8wk of age, BALB/c and CB57BL/6 inbred mice were purchased from Harlan Inc. (Indianapolis, Ind.) and housed under fluorescent light for 12 h per day. Mice were housed in cages with filter tops, and maintained in compliance with the Canadian Council on Animal Care standards.

ILK inhibitors used in the present experiments are small organic molecules, which were screened for activity as described in Example 4.

Isolation of primary mouse macrophages. Peritoneal exudate macrophages were isolated by peritoneal lavage with ice-cold sterile physiological saline 24 h after intraperitoneal injection of BALB/c and CB57BL/6 mice with 0.3 ml of sterile Zymosan A (1 mg/0.5 ml 0.9% saline). Cells were washed, resuspended in RPMI 1640 supplemented with 2 mM L-glutamine, 100 units/ml penicillin, 100 µg/ml streptomycin, and 5% FBS.

RAW 264.7 cells. RAW 264.7 cells, a murine macrophage cell line, were obtained from American Type Culture Collection (ATCC, Manassas, Va.) and cultured in DMEM supplemented with 10% FCS. Each treatment was performed in triplicate wells. RAW 264.7 cells (Balb/c background) produce a significant amount of nitric oxide upon treatment with IFN-γ alone, but require LPS for full activation. This property makes their behavior more like that of normal macrophages obtained from commonly used strains of mice.

Treatment of primary macrophages and RAW 264.7 cells. Primary macrophages ($1.5 \times 10^5$ cells/well) and RAW 264.7 ($4 \times 10^4$ cells/well) cells were grown in 96-well plates (nitrite assay), or 6-well plates ($2 \times 10^6$ cells/well) for measurement of iNOS and COX-2 expression. Following 3 h incubation, at 37 C, 5% $CO_2$ (macrophages were allowed to attach) cells were stimulated with LPS (0.5 µg/ml) and IFN-γ (100 U/ml) in the absence or presence of various concentrations of ILK inhibitors (all treatments were replicated six times). Cells were incubated for an additional 24 h, and cell free culture supernatants from each well were collected for NO and cytokine determination. The remaining cells were stained with crystal violet to determine effect of the inhibitors on cell survival.

NO production. Following stimulation, the production of NO was determined by assaying culture supernatants for $NO_2^-$, a stable reaction product of NO with molecular oxygen. Briefly, 100 µl of culture supernatant was reacted with an equal volume of Griess reagent at room temperature for 10 min. The absorbance at 550 nm was determined. All measurements were performed six times. The concentration of $NO_2^-$ was calculated by comparison with a standard curve prepared using $NaNO_2$.

Western blot analysis. After incubation with the indicated stimuli in the presence of ILK inhibitors, cells (duplicate samples, $2 \times 10^6$ cell/6-wells plate) were washed in PBS and lysed on ice in 60 µl of lysis buffer. The protein content of each sample was determined using the Bradford protein assay kit (Bio-Rad, Richmond, Calif.). Absorbance was measured at 750 nm with a Beckman DU530 spectrophotometer (Palo Alto, Calif.). Proteins were mixed with 45×SDS sample buffer. Following separation of proteins by SDS-PAGE, using 8% bis-acrylamide in the separation gel, the proteins were transferred from the gels onto PVDF membranes using a MiniProtean III Cell (Bio-Rad), at 100 V for 1.5 h. Equal amounts of protein (5 µg) were loaded onto SDS-PAGE gels and examined by Western blot analysis with anti-Actin, anti-iNOS, anti-COX-2 murine monoclonal antibodies according to the manufacturers specifications (Transduction Laboratories). Primary Abs, in 5% blocking buffer (5% NFM/TTBS), were incubated with blots 2 h or overnight at 4° C., followed by incubation with peroxidase-conjugated secondary antibody. Chemiluminescence substrates were used to reveal positive bands. The bands were exposed on x-ray films. The films are used to analyze the impact of ILK inhibitors on expression of iNOS and Cox-2 compared to various controls and "house-keeping" protein (Actin) concentration to control the protein loading and detect any non-specific effects on protein production. The Multi-Analyst/PC system from Bio-rad is being used to quantitate the bands of the expressed protein on the film. This version of Multi-Analyst is used with the Bio-Rad Gel Doc 1000 imaging system. White light is chosen as the selected light source, thus the signal strength is measured in OD (optic density) units. The OD of each band is being subtracted to a global background area of the gel.

In Vitro Angiogenesis. HUVEC cells cultured for 24 h in M199 with 0.5% FCS were plated at $6 \times 10^5$ cells/well in 12-well plates pre-coated with 300 µl of Matrigel (10.7 mg/ml; Becton Dickinson) in M199 with 0.5% FCS in the presence of VEGF (1 ng/ml), and in the absence or presence of positive control (Z)-3-[2,4-dimethyl-5-(2-oxo-1,2-dihydroindol-3-ylidenemethyl)-1H-pyrrol-3-yl]propionic acid or various ILK inhibitors. After 5 hours of incubation in a 5% $CO_2$-humidified atmosphere at 37° C., the three-dimensional organization of the cells was examined using an inverted photomicroscope. The cells were fixed with Crystal Violet (0.05% in 20% ethanol) and digitally photographed.

Enzyme immunoassays for mouse IL-6. IL-6 levels were determined with PharMingen's OptEIA ELISA set developed using an anti-mouse IL-6 Ab pair and mouse rIL-6 standard (PharMingen). Maxisorp F16 multiwell strips (Nunc, Roskilde, Denmark) were coated with anti-mouse IL-6 capture Ab (at recommended concentration) in 0.1 M $NaHCO_3$, pH 9.5, 100 µl/well, overnight at 4° C. Plates were washed three times with 0.05% Tween 20 in PBS (PBST) and blocked for 1 h at room temperature with 200 µl/well of 10% FCS in PBS (blocking and dilution buffer). Plates were washed three times with PBST and duplicate samples (100 µl/well) or standards (100 µl/well) in diluent buffer were incubated for 2 h at room temperature. Plates were washed five times with PBST and incubated with biotinylated anti-mouse IL-6 and avidin-horseradish peroxidase conjugate (at concentrations recommended by the manufacturer) for 1 h at room temperature. Plates were washed seven times with PBST and 100 µl of 3,3'5,5' tetramethylbenzidine substrate solution (TMB substrate reagent set, BD PharMingen) was added to each well. After 15-30 minute incubation at room temperature, color development was terminated by adding 50 µl of 2 N $H_2SO_4$ (Sigma). Absorbance was read at 450 nm with an EL 312e microplate reader. The lower limit of detection for IL-6 was 15.6 pg/ml.

ILK inhibitors were chosen using small molecule screening technology (KiNet™). Prior to assessing the effect of these hits in these inflammation assays, the potency, selectivity and toxicity of these compounds were determined Results Establishment of inflammation assay panel. Macrophages are important elements of innate immunity to infection and are among the first cell type in the immune response to be exposed to and activated by infectious agents. IFN-γ and LPS are potent activators of macrophages, priming them for a variety of biological effects. IFN-γ, initially secreted by NK and T cells in response to infection, converts macrophages from a resting to an activated state (inflammatory macrophages), priming them for antimicrobial activity manifested by increased killing of intracellular pathogens, and antigen processing and presentation to lymphocytes. The action of IFN-γ is synergized with the LPS second messenger, enhancing the stimulation of macrophages through the activation of NF-κB, that results in the transcriptional up-regulation of a number of genes involved in the cell-mediated immune response, including inducible iNOS. Activated macrophages are qualitatively different from quiescent macrophages. These differences are typically observed by an increased proliferation index, up-regulated expression of MHC-II, and production of various bioactive molecules. The latter biological effects are mediated by NO release and increased production of pro-inflammatory cytokines (IL-6, TNF-α, IL-1). Primary macrophages derived from Balb/c and C57BL/6 mice and RAW 264.7 cells (Balb/c background) were used to establish in vitro-inflammatory models with fast and reliable readouts.

Effects of ILK inhibitors on LPS-IFN-γ-induced NO release. To examine the effects of various ILK inhibitors on LPS-IFN-γ-induced NO release, stimulated murine macrophages were incubated in the presence of various inhibitors, at a concentration of 50 µM, over a period of 24 h. ILK inhibitors induced strong inhibition of NO production by activated macrophages. To compare the effect of the compounds across three different cell types, the NO release for each cell type was expressed relative to DMSO treated cells. The results presented in Table 1 demonstrate that the inhibitory effect of ILK inhibitors were not strain specific. For example, macrophages from Balb/c and C57BL/6 mice responded similarly to the treatment with the compounds. Although Raw 264.7 cells, compared to primary cells, were less sensitive to the treatment, they exhibited a similar pattern of response. The average values for NO release, survival and NO-inhibition are presented in Table 2.

TABLE 1

Effect of ILK inhibitors (at 50 µM) on LPS-IFN-γ - induced macrophage NO production

| | BALB/c cells | | | C57BL/6 cells | | | RAW 264.7 cells | | |
|---|---|---|---|---|---|---|---|---|---|
| | NO release (%) | Survival (%) | NO inhibition (%) | NO release (%) | Survival (%) | NO inhibition (%) | NO release (%) | Survival (%) | NO inhibition (%) |
| media | 2.3 | 75 | 0 | 3.1 | 69 | 0 | -0.3 | 119 | 0 |
| LPS - INFg | 109.9 | 88 | -25 | 130.8 | 101 | -31 | 110.2 | 91 | -21 |
| +L-NMMA 1 mM | 3.1 | 94 | 97 | 1.1 | 99 | 99 | 31.7 | 86 | 63 |
| +L-NMMA 0.5 mM | 7.9 | 97 | 92 | 8.3 | 97 | 92 | 44.2 | 92 | 52 |
| Dex 1 mM | 46.7 | 73 | 36 | 46.6 | 68 | 53 | 87.1 | 80 | -9 |
| Dex 0.5 mM | 60.6 | 84 | 28 | 67.9 | 87 | 32 | 103.6 | 98 | -6 |
| DMSO control | 100 | 100 | 0 | 100 | 100 | 0 | 100 | 100 | 0 |
| ILK HITS | | | | | | | | | |
| 15768 | 6.6 | 75 | 91 | 5.7 | 74 | 92 | 17.3 | 38 | 69 |
| 15792 | 8.2 | 88 | 91 | 5.7 | 20 | 71 | 93.5 | 69 | 7 |
| 15807 | 87.7 | 94 | 7 | 95.4 | 86 | -10 | 104.8 | 101 | 29 |
| 16207 | 0.4 | 97 | 100 | -1.5 | 16 | 109 | 4.2 | 36 | 92 |
| 16735 | -4.2 | 73 | 106 | -7.0 | 49 | 114 | 20.4 | 51 | 73 |
| 17904 | -4.4 | 84 | 105 | -6.1 | 23 | 127 | 32.6 | 46 | 51 |
| 20498 | -3.1 | 100 | 103 | -7.0 | 77 | 109 | 56.0 | 60 | 35 |
| 20533 | 46.7 | 53 | 12 | 70.5 | 88 | 20 | 92.7 | 66 | 3 |
| 20555 | 6.0 | 48 | 88 | -0.8 | 38 | 102 | 73.9 | 92 | 45 |
| 21849 | -4.2 | 41 | 110 | -8.0 | 44 | 118 | -0.1 | 51 | 100 |

Effect of ILK Inhibitors on suppression of NO production and cell survival. Twenty-four hours following treatment with the ILK inhibitors, aliquots from the cell-free supernatants were assayed for NO and IL-6 release. Surviving cells were stained and fixed (crystal violet 0.05% in 20% ethanol), to determine if the decrease in NO production was related to a decrease in cell number due to toxicity of the compounds. Percentage of survival for each cell type was calculated assuming a base line that stimulated and DMSO-treated cells demonstrate 100% survival. Only those compounds that induced strong inhibition of NO release, and caused no significant cell death were selected for further evaluation.

ILK inhibitors suppress NO production in inflammatory macrophages in a dose-dependent manner. It was demonstrated that ILK inhibitors (50 µM) decreased production of NO from activated macrophages. To determine if this effect is dose-dependent, cells were incubated in the presence of three different concentrations of inhibitors and the levels of NO in the supernatants were measured 24 h post-stimulation. The results from these experiments demonstrated that inhibitors induced a dose-dependent suppression of NO production in all three cell types. Treatment of the stimulated cells with 15807 had no effect on NO release at any of the tested concentrations, hence this compound was used as the negative control. The compounds were tested for effects on activity at concentrations of 12.5 µM, 25 µM and 50 µM.

Effect of ILK inhibitors on the LPS-IFN-γ-induced IL-6, TNFα and IL-12 release. Murine macrophages can be stimulated with LPS-IFN-γ to release several pro-inflammatory cytokines (IL-6, IL-1 and TNF-α). However, the release of any of these cytokines could be down-regulated or completely abrogated in presence of various anti-inflammatory drugs, including inhibitors of ILK. To investigate this possibility, ILK inhibitors were tested for their effects on LPS-IFN-γ-induced cytokine release. Supernatants from macrophages stimulated for 24 h with LPS-IFN-γ alone or in combination with ILK inhibitors (25 µM), were assayed for the presence of IL-6. Unstimulated macrophages release a constitutively low level of IL-6, that was noticeably up-regulated by stimulation with LPS-IFN-γ. Addition of hydrocortisone (50 µM) at the onset of the culture moderately suppressed IL-6 release. Whereas treatment of stimulated macrophages, from both mouse strains, with ILK inhibitors resulted in a very potent inhibition of IL-6 release.

Effects of ILK inhibitors on the LPS-IFN-γ-induced iNOS and COX-2 expression NO production requires that iNOS be enzymatically activity, therefore experiments were performed to examine whether the inhibitory effect of ILK inhibitors was mediated by increased iNOS protein synthesis or effects on the activity of existing enzyme. Stimulated cells were treated with ILK inhibitors (25 µM), and lysed 16 h later and a western blot analysis was performed to quantitate iNOS protein expression. Macrophages stimulated with LPS-IFN-γ synthesize and express a significant amount of iNOS protein. Addition of ILK inhibitors, however, resulted in a reduction of iNOS synthesis. The same compounds exhibited a parallel inhibitory effect on COX-2 protein expression.

ILK inhibitors down-regulate the LPS-IFN-γ-induced activation of NFκB in a dose-dependent manner. The up-regulation of iNOS expression in response to IFN-γ stimulation requires signal from a second messenger, in this case LPS (or endogenously produced TNF-α), which activators NF-κB. Two experiments were performed to determine whether treatment with ILK inhibitor affected the activation of NF-kB and to confirm a link between ILK activity and NF-κB activation, iNOS expression and NO release. The 3T3 cells were transiently transfected with a transcription reporter construct containing the NF-κB-Luc gene element, and the activity NF-kB was measured 24 h later. Transfected 3T3 cells treated with ILK inhibitors exhibited a dose-dependent decrease of NF-κB activation when compared to untreated cells (see Table 2). The reduction of transcriptional activity from the NF-κB promoter correlated with NO production.

TABLE 2

| Laboratory ID | (µM) | Inhibition (%) | Inhibition (%) |
|---|---|---|---|
| ILK inhibitors | | | |
| 15768 | 13 | 42 | 28 |
| | 25 | 29 | 17 |
| | 50 | 10 | 11 |
| 15792 | 13 | 83 | 55 |
| | 25 | 76 | 34 |
| | 50 | 54 | 26 |
| 15807 | 13 | 84 | 117 |
| | 25 | 84 | 113 |
| | 50 | 86 | 121 |
| 16207 | 13 | 62 | 26 |
| | 25 | 14 | 22 |

TABLE 2-continued

| Laboratory ID | (µM) | Inhibition (%) | Inhibition (%) |
|---|---|---|---|
| ILK inhibitors | | | |
| | 50 | 1 | 17 |
| 16735 | 13 | 68 | 17 |
| | 25 | 19 | 9 |
| | 50 | 1 | 3 |
| 17904 | 13 | 68 | 25 |
| | 25 | 49 | 23 |
| | 50 | 10 | 21 |
| 20498 | 13 | 34 | 39 |
| | 25 | 24 | 2 |
| | 50 | 8 | 1 |
| 20555 | 13 | 56 | 103 |
| | 25 | 37 | 100 |
| | 50 | 19 | 103 |
| 21849 | 13 | 42 | 23 |
| | 25 | 11 | 17 |
| | 50 | 1 | 3 |

In Vitro Angiogeneses. Angiogenesis, the development of new capillaries from pre-existing vessels, is induced by inflammation, wound healing, and a variety of immune reactions. Neovascularization is required for tumor growth and tumor progression. Recent studies have demonstrated that the COX family of enzymes plays an essential role in tumor progression and supports angiogenesis by modulating the physiology of endothelial cells. The matrigel morphogenesis assay was used to compared the effect of (Z)-3-[2,4-dimethyl-5-(2-oxo-1,2-dihydroindol-3-ylidenemethyl)-1H-pyrrol-3-yl]propionic acid (a potent inhibitor of angiogenesis) and the ILK compounds for their ability to inhibit the differentiation of HUVEC cells in vitro. ILK inhibitors demonstrated anti-angiogenic effects, blocking the growth, morphogenic organization and formation of normal capillary-like structures in the endothelial cells.

EXAMPLE 2

Figure 1:
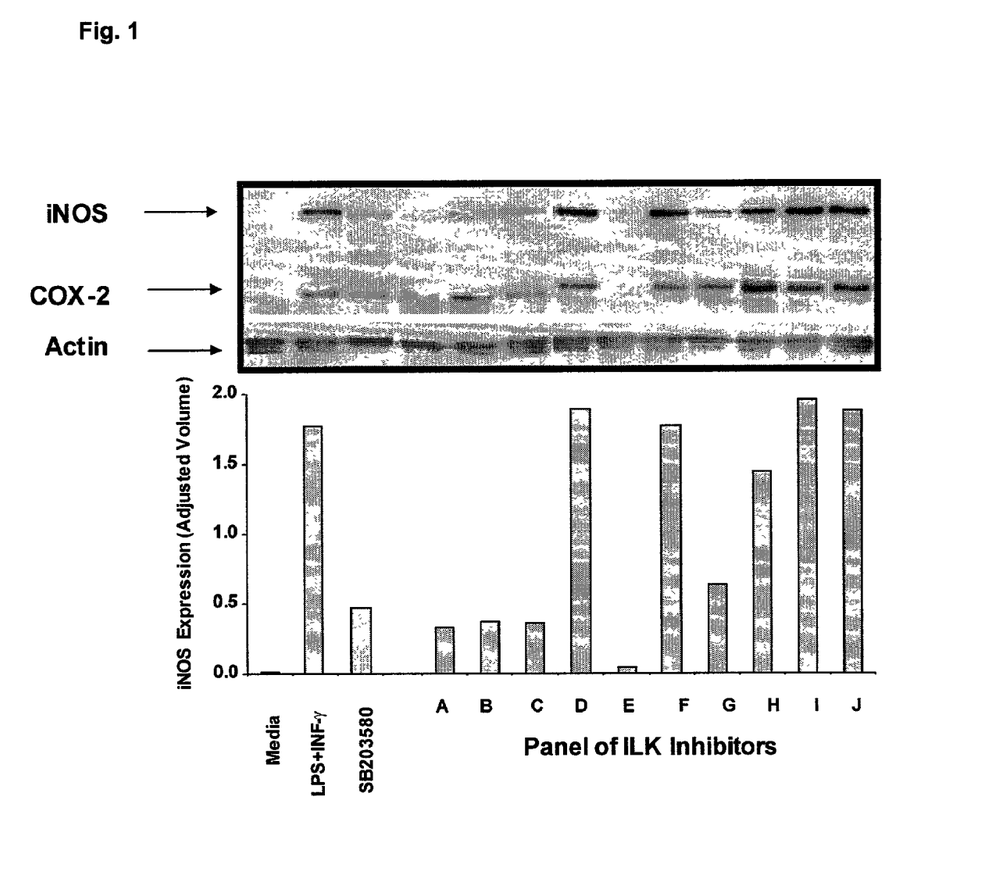
Figure 2:
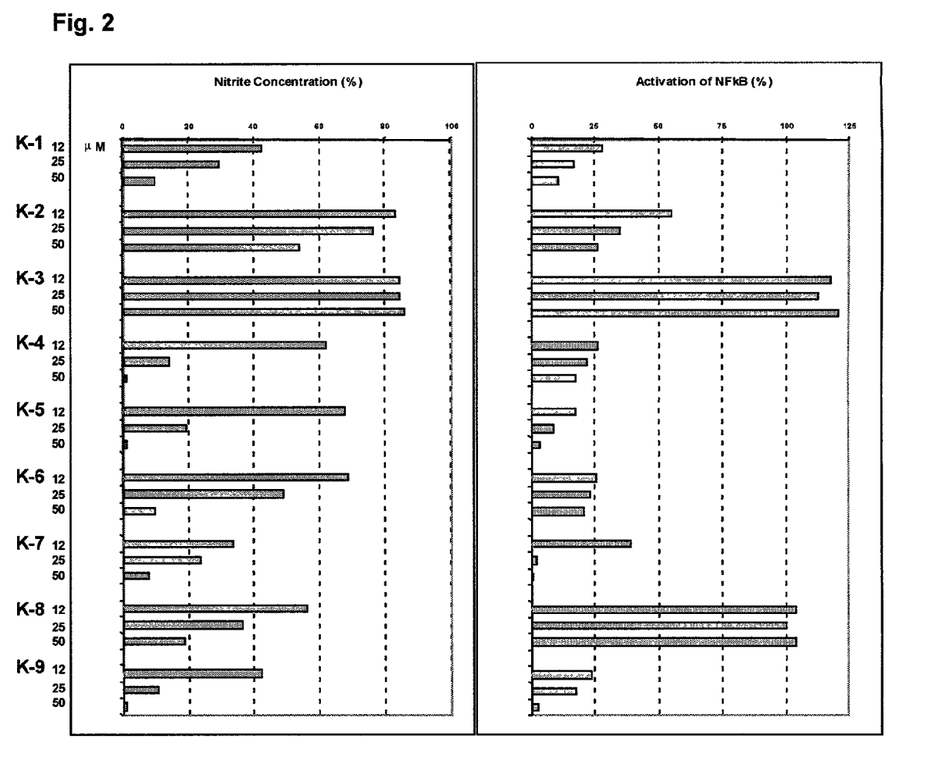
Figure 3:
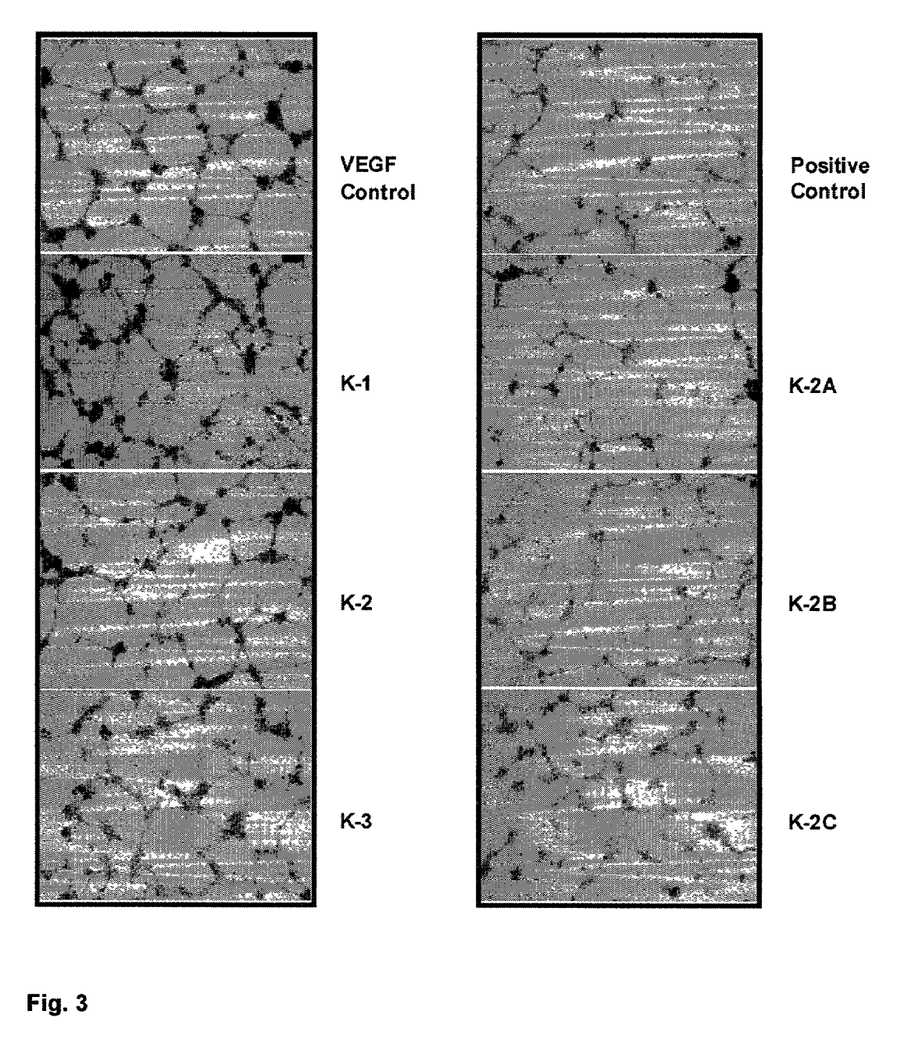

To determine the anti-angiogenic properties of ILK inhibitors, an in vitro Matrigel morphogenesis assay was established. This assay evaluates the ability of endothelial cells to differentiate into capillary-like structures, a crucial step during neovascularization. HUVEC cells when stimulated with VEGF and seeded onto Matrigel rapidly attach to the matrix and begin to migrate and interact with the extracellular matrix proteins present in the Matrigel. Within a period of 8-10 h, capillary-like structures are noticeable, and HUVEC cells demonstrate typical anastomosed cellular networks 18-20 h after plating. These capillary-like structures can be assessed by histology (FIG. 2). Samples are cut on a cross section and subsequent viewed using an electron microscope. Typically, cylindrical formations with a lumen are observed. A distinct difference in the morphology of tube formation on Matrigel, compared to other in vitro angiogenesis assays is a reduction in the proliferation of endothelial cells. Nonetheless, protein synthesis and the activities of protein kinase C and collagenase IV are still present and required for tube formation. Hence, Matrigel induces the differentiation of endothelial cells, the critical step of angiogenesis during which migration and proliferation of the cells is slowing and vascular structures begin to form. Using this model system, both inhibitors and stimulators of angiogenesis can be assessed prior to in vivo testing.

The assay was established and reproducibility confirmed. SU5416, shown to inhibit angiogenesis in other assays, was also evaluated. The ILK inhibitor KP-21849 was chosen to be assayed for its anti-angiogenic properties in this assay based on its potent anti-inflammatory effects. The results indicated that treatment of VEGF stimulated HUVEC cells with SU5146 (100 mM) did not affect endothelial cell morphogenesis, as compared to a VEGF control. However, treatment with the same concentration of KP-21849 had a profound effect on HUVEC cells, blocking the normal formation, growth and morphogenic organization of the capillary structures.

EXAMPLE 3

The anti-inflammatory properties of ILK inhibitors were assessed in an LPS and IFN-γ induced model of macrophage activation. In particular, the inhibitors were assessed for their capacity to affect NO production and IL-6 release. ILK inhibitors demonstrated an ability to block activated macrophages from producing NO and releasing IL-6, in a concentration dependent manner.

At equivalent concentrations some of the ILK compounds were more potent inhibitors of NO production and IL-6 release than dexamethasone and/or hydrocortisone. These inhibitory effects were treatment specific, as these compounds did not cause cytotoxic effects, as determined by a total protein assay after 24 h of treatment with compound.

iNOS expression is typically elevated in LPS-IFN-γ activated macrophages, and it is required that the enzyme be highly active for NO production. The ILK inhibitory compounds KP-16735 and KP-21849 significantly inhibited the expression of iNOS protein. Hence, it was concluded that ILK compounds inhibit, at least in part, LPS and IFN-γ stimulated NO production by inhibiting iNOS protein expression.

IL-6 was then assayed. Murine macrophages were stimulated with LPS (0.5 μg) IFN-γ (100 U). Supernatants from macrophages stimulated for 24 h with LPS-IFN-γ alone or in combination with ILK inhibitors (25 μM), were assayed for the presence of IL-6. As shown in Table 3 the treatment of stimulated macrophages with ILK inhibitors resulted in a very potent inhibition of IL-6 release.

TABLE 3

Effect of ILK inhibitors on the LPS-IFN-γ—induced IL-6 release in macrophages

| Laboratory ID | Inhibition of IL-6 release (%) |
|---|---|
| KP-31797 | 78 |
| KP-31798 | 31 |
| KP-31803 | 37 |
| KP-31861 | 25 |
| KP-31866 | 73 |
| KP-36716 | 31 |
| KP-36718 | 50 |
| KP-36848 | 40 |
| KP-37094 | 59 |
| KP-37130 | 33 |
| KP-37142 | 86 |
| KP-37202 | 53 |
| KP-37203 | 85 |
| KP-37204 | 63 |
| KP-37298 | 83 |
| KP-37365 | 76 |
| KP-37454 | 62 |
| KP-37516 | 55 |
| KP-37686 | 57 |
| KP-37735 | 56 |
| KP-37741 | 49 |
| KP-37756 | 41 |
| KP-47391 | 66 |
| 4-[(4-fluoro-3-trifluoromethylphenyl)hydrazono]-4H-pyrazole-3,5-diamine | 63 |

Nitric oxide and Prostaglandin $E_2$ are two pleiotropic mediators produced at inflammatory sites by the inducible enzymes iNOS and cyclooxygenase-2 (COX-2), respectively. Increased production of both mediators has been reported in acute and in chronic inflammatory diseases. In view of the above information, experiments were performed with stimulated murine macrophages to examine the ability of ILK inhibitors to down-regulate the expression of COX-2 protein. As demonstrated by western blot analysis, treatment of stimulated macrophages with the ILK inhibitors KP-16735 and KP-21849 induced a significant decrease of COX-2 protein expression. The biological activity of a selected, representative number of ILK analogs was examined in vitro on a variety of immune cells. The results show that compounds, as disclosed in U.S. Pat. No. 6,214,813, effectively suppress the release of NO and iNOS protein expression from LPS-INF-γ stimulated macrophages. In addition, most of the compounds suppressed the mitogenic responses of T-lymphocytes to Con A, suggesting direct or indirect action on lymphocytes and therefore possible immunosuppressive properties. Finally, we evaluated the in-vitro effects of compounds on production of MCP-1 chemokine by TNF-α stimulated HUVEC cells. MC-1 analogs suppressed the in vitro production of MCP-1 in a dose dependent manner. These data demonstrate that ILK inhibitors have immunomodulatory properties affecting macrophages, T lymphocyte and endothelial cell functions.

TABLE 4

ILK Inhibitors anti-inflammatory effects on a variety of cell types

| | Macrophages | | |
|---|---|---|---|
| Laboratory ID | NO (%) | INOS (%) | COX-2 (%) |
| 4-[(4-fluoro-3-trifluoromethylphenyl)hydrazono]-4H-pyrazole-3,5-diamine | 74 | 88 | 67 |
| KP-37735 | 107 | 97 | 77 |
| KP-37751 | 105 | 62 | 9 |
| KP-37755 | 104 | 69 | 40 |
| KP-47404 | 134 | 54 | 65 |
| KP-47423 | 103 | 74 | 28 |
| KP-47424 | 114 | 85 | 0 |
| KP-47435 | 110 | 67 | 44 |
| KP-47448 | 76 | 35 | 0 |
| KP-47450 | 71 | 75 | 0 |
| KP-47461 | 82 | 92 | 18 |
| KP-57063 | 114 | 99 | 37 |
| KP-57064 | 114 | 97 | 93 |

EXAMPLE 4

Production of ILK Inhibitors

Materials and Methods

Inhibition Assay: Compounds were received in lyophilized form and stored at −20° C. Stock solutions were made by weighing out the compounds and dissolving them in dimethyl sulfoxide (DMSO) to a standard concentration, usually 20 mM, and stored at −20° C. The compounds were diluted to a starting intermediate concentration of 250 μM in 1% DMSO, then serially diluted across a row of a 96 well plate using serial 2 fold dilution steps. Diluted 100% DMSO was used as a negative control.

5 μl of each compound dilution were robotically pipetted to Costar serocluster plates maintaining the same plate format. All assays consisted of the following volumes:

5 μl diluted compound

10 μl enzyme preparation

5 μl substrate
5 μl assay ATP and were then incubated 15 min at room temperature.

From each reaction, 10 μl of reaction mix was spotted onto Millipore Multiscreen-PH opaque plates and washed 2×10 min in 1% phosphoric acid. The plates were dried for at 40° C. for 30 min, then the substrate phosphate complexes were quantitated by scintillation counting. These Millipore plates are in a 96 well format with immobilized P81 phosphocellulose membranes. Both the phosphorylated and non-phosphorylated form of the substrate bind to the membrane while ATP (unincorporated phosphate) is removed in the subsequent wash steps.

Integrin Linked Kinase: The target integrin linked kinase is a full-length recombinant protein expressed in sF9 insect cells by baculovirus infection. The ILK1 substrate is CKRRRLASLR-amide.

Recombinant ILK protein was expressed using cultured insect cells and a baculovirus expression system. Standard techniques for DNA manipulation were used to produce recombinant DNA molecules and baculoviruses (Sambrook. J., Fritsch, E. F. and Maniatis, T. 1989. Molecular cloning, a laboratory manual. Second edition. Cold Spring Harbor Laboratory Press. NY; Crossen, R. and Gruenwald, S. 1998. Baculovirus expression Vector System Manual. 5th Edition. Pharmingen, San Diego, Calif.)

The ILK open reading frame (Hannigan et al., supra.), excluding the 5' and 3' untranslated regions, was inserted into the baculovirus transfer vector pAcG2T (Pharmingen) to produce a GST fusion protein under the control of the strong AcNPV polyhedrin promoter. A large scale plasmid preparation of the resulting transfer construct was made using a Qiagen Plasmid Midi Kit. This ILK transfer construct was then co-transfected with BaculoGold DNA (Pharmingen) into Sf9 insect cells (Invitrogen) and a high titre preparation of GST-ILK recombinant baculovirus was produced by amplification in Sf9 cells. Liter scale expression of GST-ILK recombinant protein was done in 1000 ml spinner flasks (Bellco) by infection of Hi5 insect cells (Invitrogen) grown in Ex-Cell 400 Serum Free Media (JRH Biosciences) at a multiplicity of infection of approximately 5. The cells were harvested three days after infection and lysed in Hypotonic Lysis Buffer (HLB; 10 mM imidazole, 5 mM EDTA, 0.1% β-mercaptoethanol, 10 ug/ml PMSF, 1 mM benzamidine) by sonication. The lysate was centrifuged at 10,000 ×g for 20 min and the supernatant was discarded. The pellet was washed twice in HLB and then washed twice in High Salt Buffer (HSB; 500 mM NaCl, 10 mM imidazole, 5 mM EDTA, 0.1% β-mercaptoethanol, 10 ug/ml PMSF, 1 mM benzamidine). The pellet was then resuspended in DNAse-ATP Buffer (DAB; 10 mM MgCl$_2$, 1 mM MnCl$_2$, β-methyl aspartic acid, 2 mM NaF, 0.55 mg/ml ATP, 1 ug/ml DNAse 1, 1% NP-40, 10 mM imidazole, 5 mM EDTA, 0.1% β-mercaptoethanol, 10 ug/ml PMSF, 1 mM benzamidine) and stirred for 30 min at room temperature, and then centrifuged at 10,000 ×g for 20 min. The pellet was resuspended in High Salt Detergent buffer (HDB; 1% NP-40, 1% Triton X-100, 500 mM NaCl, 10 mM imidazole, 5 mM EDTA, 0.1% β-mercaptoethanol, 10 ug/ml PMSF, 1 mM benzamidine), stirred for 30 min at room temperature, and then centrufuged at 10,000 ×g for 20 min. The pellet was then washed once in each of HDB, HSB, and HLB, centrifuging at 10,000 ×g each time. Finally, the pellet was resuspended in HLB.

TABLE 5

| Compound | (inhibitor concentrations in μM) | | | | | | | | | |
|---|---|---|---|---|---|---|---|---|---|---|
| | 400.0 | 160.0 | 64.0 | 25.6 | 10.2 | 4.1 | 1.6 | 0.7 | 0.3 | 0.1 |
| | % Inhibition of ILK* | | | | | | | | | |
| KP-16735 | 99 | 102 | 99 | 85 | 69 | 32 | 18 | 4 | −1 | 13 |

*percent inhibition is corrected against the maximum observed inhibition.

The compound KP-21849 inhibits ILK at 2 μM, and does not significantly inhibit SRC, GSK3β, CDC2, CK2, ERK1, and other protein kinases.

The structure of KP-21849 is:

5,6,6a,7-Tetrahydro-4H-dibenzo[de,g]quinoline-1,2,9-triol

The structure of KP-16735 is:

Another ILK inhibitor of interest has the structure:

4-[(4-fluoro-3-trifluoromethylphenyl)hydrazono]-4H-pyrazole-3,5-diamine.

What is claimed is:

1. A method of modulating the activation of monocytes in a mammalian host, the method comprising:
   administering an effective amount of an integrin-linked kinase (ILK) inhibitor, in a dose effective to inhibit said activation of monocytes; and
   monitoring said monocytes to determine inhibition of activation by determining at least one of: a decrease in monocyte expression of cycloxygenase-2 (COX-2); decrease in monocyte release of interleukin-6 (IL-6); and suppression of nuclear factor-kappa B (NF-κB) activation in monocytes; and
   wherein said ILK inhibitor inhibits ILK kinase activity in a cell-free kinase inhibition assay.

2. The method of claim 1, wherein said administration provides for a prolonged localized concentration of said ILK inhibitor.

3. The method of claim 1, wherein said host is suffering from an undesirable inflammatory response associated with said monocytes.

4. The method of claim 1, wherein monitoring said monocytes to determine inhibition of activation comprises determining a decrease in monocyte release of IL-6.

5. The method of claim 1, wherein monitoring said monocytes to determine inhibition of activation comprises determining a decrease in monocyte expression of COX-2.

* * * * *